United States Patent [19]
Aycock

[11] 3,943,166
[45] Mar. 9, 1976

[54] SEPARATION OF AN ISOMERIC MIXTURE OF ACETOXY-ALDEHYDES BY CATALYTIC DECOMPOSITION OF AN ALDEHYDE TO ACETIC ACID AND METHACROLEIN

[75] Inventor: David F. Aycock, Lenox, Mass.

[73] Assignee: General Electric Company, Pittsfield, Mass.

[22] Filed: June 21, 1973

[21] Appl. No.: 372,094

[52] U.S. Cl. ............... 260/499; 260/491; 260/540; 260/541; 260/601 R; 260/635 R; 260/635 A
[51] Int. Cl.² ......................................... C07C 67/48
[58] Field of Search ................ 260/499, 541, 601 R

[56] References Cited
UNITED STATES PATENTS
3,239,569   3/1966   Slaugh et al. ..................... 260/491

*Primary Examiner*—Vivian Garner
*Attorney, Agent, or Firm*—Donald M. Papuga; William F. Mufatti

[57] ABSTRACT

A process for separating 2-methyl-3-acetoxypropionaldehyde from an isomeric mixture of aldehydes by catalytic decomposition.

3 Claims, No Drawings

SEPARATION OF AN ISOMERIC MIXTURE OF ACETOXY-ALDEHYDES BY CATALYTIC DECOMPOSITION OF AN ALDEHYDE TO ACETIC ACID AND METHACROLEIN

BACKGROUND OF THE INVENTION

It is known in the art that an ester when heated at 300°–550°C. decomposes into an olefin and a carboxylic acid. The reaction may be carried out in either the liquid or the vapor phase, by simply heating the ester in a metal bath or with a free flame or by passing the compound through an electrically heated tube.

Also, it is known that dehydration of β-hydroxyaldehydes is a facile reaction catalyzed by many materials such as acids, bases, alumina, etc. Separation of a particular acetoxyaldehyde from an isomeric mixture of acetoxyaldehydes is difficult since the catalyst in many instances will react with the acetoxyaldehydes. However, it has been discovered that a particular acetoxyaldehyde may be decomposed by an elimination catalyst without reacting with the other acetoxyaldehydes.

DESCRIPTION OF THE INVENTION

This invention is concerned with a process for separating 2-methyl-3-acetoxypropionaldehyde from an isomeric mixture of 4-acetoxybutyraldehyde, 2-methyl-3-acetoxypropionaldehyde and 2-acetoxybutyraldehyde which comprises heating said isomeric mixture in the presence of an elimination catalyst which decomposes the 2-methyl-3-acetoxypropionaldehyde to acetic acid and methacrolein and separating the acetic acid and methacrolein therefrom, said elimination catalyst being selected from the group consisting of a tertiary amine, silica-aluminas and zeolites.

The isomeric aldehydes of the present invention are produced by the hydroformylation of allyl acetate which is disclosed in an application of William E. Smith, entitled "A Process for the Production of Butanediol," Ser. No. 365,228, filed May 30, 1973 and assigned to the same assignee as the present invention. Also, this application of Smith discloses hydrogenating these aldehydes to produce a mixture comprising the acetate esters of the corresponding butanediols. This mixture of the acetate esters of butanediols is then de-esterified to produce a mixture of diols. 1,4-butanediol is useful in making polyester resins with dicarboxylic acids.

The 2-methyl-3-acetoxypropionaldehyde of the instant invention has a boiling point which lies between the boiling points of 4-acetoxybutyraldehyde and 2-acetoxybutyraldehyde. This makes separation of an isomeric mixture of 4-acetoxybutyraldehyde, 2-methyl-3-acetoxypropionaldehyde and 2-acetoxybutyraldehyde difficult. Also, this makes difficult the separation of the isomeric diols which are produced from hydrogenation of the isomeric aldehydes followed by de-esterification, since a diol corresponding to 2-methyl-3-acetoxypropionaldehyde would be formed which has a boiling point between the diol corresponding to 2-acetoxybutyraldehyde and the diol corresponding to 4-acetoxybutyraldehyde. The two products, i.e., acetic acid and methacrolein, obtained by decomposing 2-methyl-3-acetoxypropionaldehyde, have a high volatility and are easily removed by distillation from the mixture of 4-acetoxybutyraldehyde, 2-acetoxybutyraldehyde, acetic acid and methacrolein.

Also, this invention is concerned with a process for separating 2-methyl-3-acetoxypropionaldehyde from an isomeric mixture of 4-acetoxybutyraldehyde, 2-methyl-3-acetoxypropionaldehyde and 2-acetoxybutyraldehyde by heating said mixture in the presence of an elimination catalyst which decomposes the 2-methyl-3-acetoxypropionaldehyde to acetic acid and methacrolein without reacting with either the 4-acetoxybutyraldehyde or the 2-acetoxybutyraldehyde.

The elimination catalyst which may be employed within the scope of this invention is selected from the group consisting of a tertiary amine, silica-aluminas and zeolites. The tertiary amines which may be used include alkylamines, arylamines, cycloalkylamines, alkarylamines and aralkylamines of 1 to 25 carbon atoms as well as heterocyclic amines. Examples of tertiary amines which may be used include trimethylamine, triethylamine, tri-n-propylamine, tri-n-butylamine, tri-n-amylamine, tribenzylamine, propyldimethylamine, methyldiethylamine, butyldimethylamine, t-butyldimethylamine, pentyldimethylamine, methylethylbutylamine, heptyldimethylamine, nonyldimethylamine, tetradecyldimethylamine, tricyclohexylamine, triphenylamine, pyridine, etc.

The silica-aluminas which may be used vary in composition from pure silica to pure alumina.

The zeolites of the instant invention include both the natural zeolites and the alkali metal aluminosilicates or the commercial zeolites, also known as molecular sieves. These zeolites are well known in the art and are detailed in "Molecular Sieves," Charles K. Hersh, Reinhold Publishing Company, New York (1961) which is incorporated herein by reference. preferably, representative natural zeolites which may be employed in the instant invention include those in Table 3-1, on page 21 of the Hersh reference while representative molecular sieves include those in Table 5-1, on page 54 of the Hersh reference. A most preferred molecular sieve is a Davison Molecular Sieve Type 3A which has a silica-alumina base with potassium as the cation.

The catalyst may be added along with the isomeric aldehydes into a reaction zone. A preferred amount of catalyst is about from 0.5% to about 2% based on weight of the isomeric aldehydes. If the catalyst is a molecular sieve or silica-aluminas, the reactants are flowed through the molecular sieve or silica-alumina in a reaction zone.

The temperature at which the reaction proceeds can be varied widely. Temperatures ranging from about 90° to 180°C. are generally adequate although higher temperatures can be used.

Although atmospheric pressures are the only ones normally required, it will be of course apparent to those skilled in the art that superatmospheric pressure or subatmospheric pressure may be used where conditions and concentrations so dictate.

DESCRIPTION OF THE PREFERRED EMBODIMENT

The following Examples are set forth to illustrate more clearly the principle and practice of this invention to those skilled in the art. Unless otherwise specified, where parts or percents are mentioned, they are parts or percents by weight.

EXAMPLE I 0.3 g. of triethylamine is added to an 18.0 g. mixture containing (by weight) 4-acetoxybutanaldehyde (69%), 2-acetoxybutanaldehyde (10%) and 2-methyl-3-acetoxypropionaldehyde (15%). (the mixture of aldehyde isomers obtained from the hydroformylation reaction of allyl acetate). The mixture is heated at 95°C. in a flask equipped with a reflux condenser. Analysis shows that within 25 minutes 2-methyl-3-acetoxypropionaldehyde is completely converted into methacrolein and acetic acid. The other two aldehyde isomers remained unchanged. Methacrolein and acetic acid are separated from the aldehyde isomers by distillation.

EXAMPLE II 1.0 g. of activated alumina ⅛ inch pellets is added to a 10.0 g. mixture containing (by weight) 4-acetoxybutanaldehyde (69%), 2-acetoxybutanaldehyde (10%) and 2-methyl-3-acetoxypropionaldehyde (15%). The mixture is heated at 125°C. in a flask equipped with a reflux condenser. Analysis shows that within 20 minutes 2-methyl-3-acetoxypropionaldehyde is completely converted into methacrolein and acetic acid. The other two aldehyde isomers remain unchanged. Methacrolein and acetic acid are separated from the aldehyde isomers by distillation.

EXAMPLE III

A jacketed stainless steel column 127 cm. long and 1.9 cm. in diameter is packed with a zeolite molecular sieve. The column is heated to 150°C. and a mixture containing (by weight) 4-acetoxybutanaldehyde (57%), 2-acetoxybutanaldehyde (8%), 2-methyl-3-acetoxypropionaldehyde (13%) and water (16%) is pumped through the column at a rate of 7 ml./minute. Approximately 22 liters are passed through the column. Analysis shows that, in the product stream, 2-methyl-3-acetoxypropionaldehyde is completely converted into methacrolein and acetic acid and the other two aldehyde isomers remain unchanged. Methacrolein and acetic acid are separated from the aldehyde isomers by distillation.

It should, of course, be apparent to those skilled in the art that changes may be made in the particular embodiments of the invention described which are within the full intended scope of the invention as defined by the appended claims.

What is claimed is:

1. A process for separating 2-methyl-3-acetoxypropionaldehyde from an isomeric mixture of 4-acetoxybutyraldehyde, 2-methyl-3-acetoxypropionaldehyde and 2-acetoxybutyraldehyde which comprises heating at a temperature of from about 90° to about 180°C said mixture in the presence of an elimination catalyst which decomposes the 2-methyl-3-acetoxypropionaldehyde to acetic acid and methacrolein, and separating the acetic acid and methacrolein therefrom by distillation; said elimination catalyst being selected from the group consisting of a tertiary amine, silica-aluminas of from pure silica to pure alumina and zeolites; wherein the tertiary amine is selected from the group consisting of alkylamines, arylamines, cycloalkylamines, alkarylamines, aralkylamines of 1 to 25 carbon atoms and heterocyclic amines.

2. The process of claim 1 wherein the tertiary amine is pyridine.

3. The process of claim 1 wherein the tertiary amine is triethylamine.

* * * * *